(12) United States Patent
Kohler et al.

(10) Patent No.: US 8,133,509 B2
(45) Date of Patent: Mar. 13, 2012

(54) HYDROGELS BASED ON ALIPHATIC NCO PREPOLYMERS

(75) Inventors: Burkhard Kohler, Zierenberg (DE); Michael Mager, Leverkusen (DE); Stefanie Eiden, Leverkusen (DE); Johan Kijlstra, Odenthal (DE)

(73) Assignee: Bayer MaterialScience AG, Leverkusen (DE)

( * ) Notice: Subject to any disclaimer, the term of this patent is extended or adjusted under 35 U.S.C. 154(b) by 424 days.

(21) Appl. No.: 11/977,278

(22) Filed: Oct. 24, 2007

(65) Prior Publication Data

US 2008/0102126 A1  May 1, 2008

(30) Foreign Application Priority Data

Oct. 27, 2006 (DE) .................. 10 2006 050 793

(51) Int. Cl.
| | |
|---|---|
| *A01N 59/06* | (2006.01) |
| *A61K 33/12* | (2006.01) |
| *A61K 9/00* | (2006.01) |
| *A61K 33/30* | (2006.01) |
| *A61K 33/34* | (2006.01) |
| *A61K 33/38* | (2006.01) |
| *A61K 6/083* | (2006.01) |
| *A61K 8/72* | (2006.01) |
| *A61F 13/00* | (2006.01) |
| *A61P 17/02* | (2006.01) |
| *A61P 31/04* | (2006.01) |

(52) U.S. Cl. ........ 424/486; 424/618; 424/630; 424/642; 523/105

(58) Field of Classification Search .................. 424/683
See application file for complete search history.

(56) References Cited

U.S. PATENT DOCUMENTS

| | | | | |
|---|---|---|---|---|
| 4,118,354 | A | * 10/1978 | Harada et al. | 524/711 |
| 4,576,718 | A | * 3/1986 | Reischl et al. | 210/616 |
| 5,059,424 | A | 10/1991 | Cartmell et al. | 424/443 |
| 5,112,618 | A | 5/1992 | Cartmell et al. | 424/443 |
| 5,115,801 | A | 5/1992 | Cartmell et al. | 602/48 |
| 5,175,229 | A | * 12/1992 | Braatz et al. | 528/48 |
| 5,204,110 | A | 4/1993 | Cartmell et al. | 424/443 |
| 5,849,368 | A | * 12/1998 | Hostettler et al. | 427/536 |
| 6,180,132 | B1 | 1/2001 | Huang et al. | 424/445 |
| 6,238,691 | B1 | 5/2001 | Huang et al. | 424/443 |
| 6,448,364 | B1 | * 9/2002 | Clatty et al. | 528/61 |
| 6,861,067 | B2 | 3/2005 | McGhee et al. | 424/445 |
| 2001/0026810 | A1 | 10/2001 | McGhee et al. | 424/486 |

FOREIGN PATENT DOCUMENTS

| | | |
|---|---|---|
| EP | 0177289 | 4/1986 |
| EP | 0454930 | 11/1991 |
| EP | 0460328 | 12/1991 |
| JP | 2001 261841 | * 3/2000 |
| JP | 2001-261841 | 9/2001 |
| KR | 2001092463 A | * 10/2001 |
| WO | WO-02/060501 | 8/2002 |

* cited by examiner

*Primary Examiner* — Fereydoun G Sajjadi
*Assistant Examiner* — Audrea Buckley
(74) *Attorney, Agent, or Firm* — Connolly Bove Lodge & Hutz LLP

(57) ABSTRACT

The invention concerns novel hydrogels, a process for the preparation of these hydrogels and would contact materials comprising these hydrogels. These polyurethane hydrogels are obtained by the reaction of aliphatic isocyanate prepolymers with polyols comprising tertiary nitrogen in water.

8 Claims, No Drawings

HYDROGELS BASED ON ALIPHATIC NCO PREPOLYMERS

CROSS REFERENCE TO RELATED PATENT APPLICATION

The present patent application claims the right of priority under 35 U.S.C. §119 (a)-(d) of German Patent Application No. 110 2006 050 793.2, filed Oct. 27, 2006.

BACKGROUND OF THE INVENTION

The invention relates to novel hydrogels, a process for preparing these hydrogels and wound contact materials comprising these hydrogels. The hydrogels herein are obtained by the reaction of aliphatic isocyanate prepolymers with polyols comprising tertiary nitrogen in water.

Hydrogels are typically water-containing gels (i.e. shape-stable, easily deformable, disperse systems rich in liquids and gases and comprising at least two components which usually consists of a colloidally divided solid having long or highly branched particles and a liquid (usually water) as a dispersion medium) based on hydrophilic but water-insoluble polymers, in the form of three-dimensional networks. These networks swell up in water to an equilibrium volume while substantially retaining their shape. Network formation takes place predominantly via chemical linking of the individual chains of polymer, but is also possible physically through electrostatic, hydrophobic or dipole-dipole interactions between individual segments of the polymer chains. Desired properties for the hydrogels can be specifically set via the choice of monomers used for polymer construction, the type of crosslinking and the crosslink density. Hydrogels are typically based on poly(meth)acrylic acids, poly(meth)acrylates, polyurethanes, polyvinylpyrrolidone or polyvinyl alcohol. They are generally highly compatible with living tissues and therefore are often used as biomaterials, and particularly in the biomedical and pharmaceutical sector.

Polyurethane hydrogels, produced from hydrophilic NCO prepolymers, are known per se. Such polyurethane hydrogels are described in, for example, EP-A 426 422, EP-A 455 324, WO 98/17215, WO 99/13923 and WO/2002/060501. They are used in the medical treatment of wounds, for example as wound contact materials. These polyurethane hydrogels have the advantage of providing a controlled way to keep (dry) wounds moist, which is beneficial for wound healing. Polyurethane hydrogels generally have very good mechanical properties.

Polyurethane hydrogels are generally produced from an isocyanate component and polyethylene glycol, propylene glycol or glycerol as polyol, partly in the presence of oligoalkylene oxides having primary amino end groups as accelerant and water for hydrolysis. Irrespective of whether an accelerant is or is not used, the polyol component is always used in excess, so that the hydrogels thus obtained still contain excess polyol with or without accelerant. Furthermore, the reaction times in relation to gel formation are very slow. The gel point, even in the case of the variants where an accelerant is included, takes more than 90 minutes to reach, which is followed by a supplementary reaction over several hours. The hydrogels are described with and without antimicrobially active substances.

The present invention therefore has as an object to provide novel polyurethane hydrogels which have improved gel-formation and which are free of unreacted starting compounds such as isocyanate, polyol and/or accelerant. These hydrogels shall be obtainable from very few components and contain complexing, non-isocyanate-reactive groups such that the incorporation of metals or metal ions as antimicrobial actives may be possible.

It has now been found that this object is achieved by a specific process of production.

SUMMARY OF THE INVENTION

The present invention accordingly provides a process for producing hydrogels and the resulting hydrogels.

The process for producing the polyurethane hydrogels comprises reacting:
a) one or more nonionically hydrophilicized, aliphatic and/or cycloaliphatic polyisocyanate prepolymer which contains less than 1% by weight of monomeric diisocyanates, with
b) one or more compounds having at least one tertiary amino group and at least three hydroxyl groups,
c) water,
and, optionally,
d) one or more antimicrobially active metal salts and/or metal particles.

The polyurethane hydrogels of the invention comprise the reaction product of:
a) one or more nonionically hydrophilicized, aliphatic and/or cycloaliphatic polyisocyanate prepolymer which contains less than 1% by weight of monomeric diisocyanates, with
b) one or more compounds having at least one tertiary amino group and at least three hydroxyl groups,
c) water,
and, optionally,
d) one or more antimicrobially active metal salts and/or metal particles.

DETAILED DESCRIPTION OF THE INVENTION

Suitable compounds to be used as component a) in accordance with the present invention include any polyisocyanate prepolymers known per se to one skilled in the art, which on average contain two or more free NCO groups and in addition are based on aliphatic and/or cycloaliphatic mono-, di- and/or triisocyanates, as well as having one or more oxyethylene groups for nonionic hydrophilicization.

It is preferred that the polyisocyanate prepolymers used as component a) have polyoxyalkylene units attached via urethane groups, and preferably at least 60 wt %, more preferably at least 70 wt % and most preferably at least 80 wt % of the oxyalkylene units attached therein are oxyethylene units.

It is preferred that the oxyethylene units are present therein in the form of blocks.

Suitable polyisocyanate prepolymers are obtainable in a conventional manner by reaction of, for example, polyether diols with mono-, di- and/or triisocyanates, and/or their higher molecular weight ascendant products which contain uretidione, isocyanurate, allophanate, biuret, iminooxadiazinedione and/or oxadiazinetrione structures. If appropriate, additional mono-, di- or polyols can be used as building block components.

The starting monomeric isocyanates suitable herein can be any isocyanates which are obtainable through phosgenation or by phosgen-free processes, for example, by thermal urethane scissioning, and which have aliphatically, cycloaliphatically and/or araliphatically attached isocyanate groups. Suitable monomeric isocyanates include compounds such as 1,4-diisocyanatobutane, 1,6-diisocyanatohexane (HDI), 2-methyl-1,5-diisocyanatopentane, 1,5-diisocyanato- 2,2-dimethylpentane, 2,2,4- or 2,4,4-trimethyl-1,6-diisocyanatohexane, 1,10-diisocyanatodecane, 1,3- and 1,4-diisocyanatocyclohexane, 1,3- and 1,4-bis(isocyanatomethyl)cyclohexane, 1-isocyanato-3,3,5-trimethyl-5-isocyanatomethylcyclohexane (isophorone diisocyanate, IPDI), 4,4'-diisocyanatodicyclohexylmethane, 1-isocyanato-1-methyl-4(3)isocyanatomethylcyclohexane, bis(isocyanatomethyl)norbornane or any mixtures thereof.

The suitable polyether diols for preparing the polyisocyanate prepolymers are obtainable in a conventional manner under KOH and/or double metalcyanide (DMC)-catalysis by the addition of cyclic ethers such as alkylene oxides onto OH- and/or NH-functional starters. The addition can take place blockwise or randomly, with blockwise addition being preferred.

Preferred cyclic ethers are alkylene oxides, more preferably ethylene oxide and if appropriate propylene oxide.

The NCO/OH ratio in the production of the polyisocyanate prepolymers is preferably in the range from 1.6:1 to 30:1, more preferably in the range from 4:1 to 12:1 and most preferably in the range from 4:1 to 10:1.

The prepolymers preferably have an NCO group content in the range from 1.5% to 3.5% by weight.

The residual level of monomeric diisocyanates present in the prepolymers which are used as component a) is less 1% by weight, preferably less than 0.5% by weight, and more preferably less than 0.1% by weight. This is typically achieved by prepolymer production in the presence of an excess of the isocyanate component, and subsequent distillative removal of unconverted diisocyanates by film distillation.

In principle, the prepolymer production can also be carried out in the presence of conventional catalysts such as amines or tin compounds, and also stabilizers such as benzoyl chloride, isophthaloyl chloride, dibutyl phosphate or methyl tosylate.

In accordance with the present invention, the compounds having at least one tertiary amino group and at least three hydroxyl group that are used as component b) preferable have a miscibility with water at 25° C. of at least 2% by weight, based on 100% by weight of the resulting mixture. More preferably, these compounds are miscible with water at 25° C. in any proportion to yield a homogeneous and clear mixture.

It is particularly preferable that the compounds having at least one tertiary amino group and at least three hydroxyl group which are used as component b) herein, in addition to having the aforementioned properties, correspond to one of two general formulas. These two general formulas are set forth below:

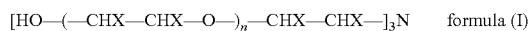
[HO—(—CHX—CHX—O—)$_n$—CHX—CHX—]$_3$N   formula (I)

and

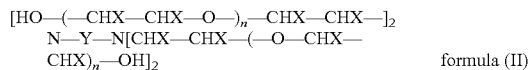
[HO—(—CHX—CHX—O—)$_n$—CHX—CHX—]$_2$
N—Y—N[CHX—CHX—(—O—CHX—
CHX)$_n$—OH]$_2$   formula (II)

wherein:
n represents a natural number from 0 to 10, preferably from 0 to 2,
each X independently represents a hydrogen atom or a methyl radical, and preferably a hydrogen atom or alternatingly in the chain a hydrogen atom and a methyl radical,
and
Y represents a $C_2$-$C_6$-alkylene radical, a $C_5$-$C_{22}$-cycloalkylene radical or a $C_6$-$C_{12}$-arylene radical, and preferably an ethylene radical.

Examples of such compounds which are suitable to be used as component b) herein are aminoalcohols such as, for example, triethanolamine or tripropanolamine, or are polyalkylene oxides started on ammonia, di- or polyamines or aminoalcohols.

The equivalent weight of the compounds suitable to be used as component b), based on the hydroxyl groups is preferably in the range from 49.6666 to 150 g/eq.

In the hydrogels of the invention, components a) and b) are preferably used in amounts such that the NCO/OH ratio is in the range of from 2:1 to 0.7:1 and more preferably in the range from 1.5:1 to 0.8:1.

Component c) water is used in amounts such that satisfactory gel-formation is achieved. It is preferred to use from 2 to 50 parts by weight of water, and more preferably from 4 to 19 parts by weight of water, per one part by weight of the combined weight of compounds a) and b).

If desired, metal salts and/or metal particles in the form of aqueous or alcoholic solutions or sols can be included to provide an antimicrobial finish to the hydrogels, for example. Preferably, the polyurethane hydrogels are admixed with metal particles such as, for example, metal particles comprising one or more of Ag, Cu, Zn or alloys containing these metals.

To permit homogeneous incorporation, these metal particles are preferably nanoparticulate and have an average particle size, as determined by laser correlation spectroscopy, of 5 to 200 nm and preferably of 10 to 60 nm.

When metal particles are present in the hydrogels, they are present in amounts of up to 5 parts by weight, based on the total weight of compounds used in components a) and b), with the sum of the total weight of components a) and b) totalling 100 parts by weight.

Silver particles are preferred metal particles of the aforementioned kind.

If Ag particles with an average particle size of 10 to 60 nm are used, yellow to orange but still transparent hydrogels are obtained.

Preferred silver particles in the form of aqueous sols contain from 0.05% to 5% by weight of silver, and preferably 0.08% to 2% by weight of silver (based on the wt. of the aqueous sols).

These active metal salts and/or metal particles suitable for use as component d) herein are obtained, for example, by presenting a silver nitrate solution as an initial charge and adding the equimolar amount of NaOH dissolved in water with the aid of a dispersing assistant, such as polyvinylpyrrolidone. The subsequent reduction is effected by means of a reducing agent, such as formaldehyde.

The hydrogels of the invention are preferably produced by premixing the components b) and c) and also if appropriate, d). Subsequently, component a) is added with stirring to the premixture of components b), c) and optionally d).

The temperature at which the process of the present invention is carried out is preferably in the range of from 5 to 50° C., more preferably in the range of from 10 to 45° C. and most preferably in the range of from 15 to 25° C.

In addition to components a) through d) as described above, further additives can also be added to the hydrogels. Such additives include, for example, antibiotics, essential oils, odorants and/or fungicides. In the present invention, it is preferable to introduce water-soluble substances into the hydrogel via the aqueous phase and to introduce oil-soluble substances into the hydrogel via the prepolymer, i.e. component a).

The hydrogels of the present invention are particularly useful as a wound contact material. The hydrogel can be further converted e.g. by lamination, for example with a backing of a foil.

The following examples further illustrate details for the preparation and use of the compositions of this invention. The invention, which is set forth in the foregoing disclosure, is not to be limited either in spirit or scope by these examples. Those skilled in the art will readily understand that known variations of the conditions and processes of the following preparative procedures can be used to prepare these compositions. Unless otherwise noted, all temperatures are degrees Celsius and all parts and percentages are parts by weight and percentages by weight, respectively.

EXAMPLES

Viscosities were measured at 23° C. using a plate-cone viscometer from Anton Parr.

Example 1

Production of Nanosilver

Production of $Ag_2O$ Nuclei:

A 54 millimolar solution of silver nitrate (9.17 g/l $AgNO_3$) was prepared as reactant 1 and a 54 millimolar solution of NaOH (2.14 g/l) having a dispersant concentration of 10 g/l was prepared as reactant 2. The solvent used was demineralized water (prepared using Milli-Qplus, QPAK☐2, Millipore Corporation). The dispersant used was PVP K15 polyvinylpyrrolidone (commercially available from Fluka Chemie GmbH, DE). 250 ml of reactant 1 were introduced as initial charge into a glass beaker at room temperature. 250 ml of reactant 2 were added to the reactant solution at a uniform rate over 10 s with continued stirring. The equivalent ratio of base to silver salt in the reactant mixture is thus 1.0. The batch was then subsequently stirred for a further 10 min to obtain a greyish black colloid-chemically stable $Ag_2O$ nanosol.

Reduction of $Ag_2O$ Nuclei to Metallic Particles of Silver

The 500 ml of $Ag_2O$ nanosol produced in Example 1 were admixed with 25 ml of a 2.33 molar aqueous formaldehyde solution (70 g/l) added at room temperature with continuous stirring, stored at 60° C. for 30 min and cooled down to obtain a colloid-chemically stable sol comprising metallic nanoparticles of silver and having a silver content of 1.16%. Subsequently, the particles were isolated by centrifugation (for 60 min at 30 000 rpm, using an Avanti J 30i, Rotor JA 30.50, Beckman Coulter GmbH) and redispersed in 630 ml of demineralized water by ultrasonication (using a Branson Digital Sonifier). A colloid-chemically stable Ag nanosol having a solids content of 0.92% by weight and a pH of 7.4 was obtained.

Investigation of the particle size by dynamic light scattering revealed crystalline Ag particles having an effective hydrodynamic diameter of 46 nm.

Example 2

Example 1 was repeated except that the Ag particles were not centrifuged off and redispersed in water.

Example 3

A mixture of 200 g of hexamethylene diisocyanate (HDI) and 1 g of benzoyl chloride was presented as initial charge at 80° C., 400 g of a polyethylene oxide-co-propylene oxide started on trimethylolpropane (TMP) and having an ethylene oxide content of 63% and an OH number of 36 mg KOH/g were added over 2 h, and the mixture was stirred at 80° C. for 1 h. The excess HDI was removed by film distillation at 130° C. and 0.5 Torr. The result was a prepolymer having an NCO content of 2.4% by weight and a viscosity of 4460 mPas.

Example 4

A mixture of 200 g of hexamethylene diisocyanate (HDI), 1 g of benzoyl chloride and 1 g of methyl tosylate was presented as initial charge at 80° C., 400 g of a polyethylene oxide-co-propylene oxide started on trimethylolpropane (TMP) and having an ethylene oxide content of 80% and an OH number of 29 mg KOH/g were added over 2 h, and the mixture was stirred for 1 h. The excess HDI was removed by film distillation at 130° C. and 0.5 Torr. The result was a prepolymer having an NCO content of 2.3% by weight and a viscosity of 6070 mPas.

Example 5

A mixture of 200 g of isophorone diisocyanate (IPDI), 1 g of benzoyl chloride and 1 g of methyl tosylate was presented as initial charge at 80° C., 400 g of a polyethylene oxide-co-propylene oxide started on trimethylolpropane (TMP) and having an ethylene oxide content of 80% and an OH number of 29 mg KOH/g were added over 2 h, and the mixture was stirred for 1 h. The excess IPDI was removed by film distillation at 130° C. and 0.5 Torr. The result was a prepolymer having an NCO content of 2.4% by weight and a viscosity of 8800 mPas.

Example 6

7 g of water, 1 g of a silver sol (produced according to Example 1; diluted with demineralized water to ten times the volume) and 0.06 g of triethanolamine were mixed and admixed with 2 g of the prepolymer according to Example 3 to obtain after just 3 min a transparent, orange hydrogel.

Example 7

7 g of water, 1 g of a silver sol (produced according to Example 1) and 0.06 g of triethanolamine were mixed and admixed with 2 g of the prepolymer according to Example 3 to obtain after just 3 min a dark brown but transparent hydrogel.

Example 8

Example 6 was repeated except that the silver sol of Example 2 was used after dilution with demineralized water to ten times the volume. After 3 min, a transparent, orange hydrogel was obtained.

Example 9

Example 8 was repeated except that the silver sol of Example 2 was used. After 3 min, a dark brown but transparent hydrogel was obtained.

Example 10

18 g of water and 0.12 g of an ethylenediamine-started polypropylene oxide having an OH number of 468 were mixed and admixed with 2 g of the prepolymer according to Example 4. A transparent, colorless hydrogel was obtained after 4 min. The NCO:OH ratio was 1.10:1.

Example 11

19 g of water and 0.06 g of an ethylenediamine-started polypropylene oxide having an OH number of 468 were mixed and admixed with 1 g of the prepolymer according to Example 5. A transparent, colorless hydrogel was obtained after 5 min. The NCO:OH ratio was 1.14:1.

Comparative Example 1 According to WO 2002060501

Mixtures were prepared from 10 g of prepolymer from Example 3 with 10 g of polyethylene glycol 400 ($M_n$=400, Sigma-Aldrich, USA) on the one hand, and on the other, of 30 g of demineralized water with 10 g of propylene glycol and 0.5 g of Jeffamine D400 ($M_n$=400, difunctional, Huntsman, Belgium). The two parts were combined and formed a hydrogel after 45 min. The NCO:OH ratio of 32:1 in this hydrogel means that, after the reaction, almost the entire quantity of propylene glycol was present in unreacted form, and thus remained as a low molecular weight, unattached plasticizer in the hydrogel at about 16% by weight.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for producing polyurethane hydrogels comprising mixing:
   a) one or more nonionically hydrophilicized, aliphatic and/or cycloaliphatic polyisocyanate prepolymers which contain less than 1% by weight of monomeric diisocyanates,
   b) one or more compounds having at least one tertiary amino group and at least three hydroxyl groups,
   c) water, and, optionally,
   d) one or more antimicrobially active metal salts and/or metal particles
   wherein said polyisocyanate prepolymers comprise polyoxyalkylene units attached via urethane groups, wherein at least 60 weight % of the oxyalkylene units of said polyoxyalkylene units are oxyethylene units, wherein said oxyethylene units are present in the form of blocks.

2. The process of claim 1, wherein at least 80 weight % of the oxyalkylene units of said polyoxyalkylene units are oxyethylene units.

3. The process of claim 1, wherein a) said polyisocyanate prepolymers have an NCO group content of from 1.5% to 3.5% by weight.

4. The process of claim 1, wherein a) said polyisocyanate prepolymers have a residual content of less than 0.1% by weight of monomeric diisocyanates.

5. The process of claim 1, in which b) said one or more compounds having at least one tertiary amino group and at least three hydroxyl groups correspond to one of the general formulas:

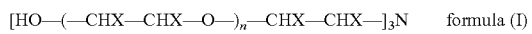

or

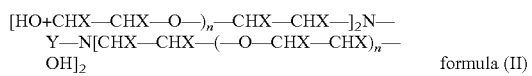

wherein:
   n represents a natural number from 0 to 10,
   each X: independently represents a hydrogen atom or a methyl radical, and preferably X represents a hydrogen or alternatingly in the chain a hydrogen atom and a methyl radical,
   and
   Y represents a $C_2$-$C_6$-alkylene radical, a $C_5$-$C_{22}$-cycloalkylene radical or a $C_6$-$C_{12}$-arylene radical.

6. The process of claim 1, wherein components a) and b) are present in amounts such that the NCO/OH ratio is in the range of from 2:1 to 0.7:1.

7. The process of claim 1, wherein from 4 to 19 parts by weight of component c) water are present, per one part by weight of the combined weight of the components a) and b).

8. The process of claim 1, in which d) said active metal salts and/or metal particles are added in the form of aqueous or alcoholic solutions or sols, and comprise at least one of the elements Ag, Cu, Zn or alloys thereof.

* * * * *